(12) United States Patent
Sachs et al.

(10) Patent No.: US 8,421,021 B2
(45) Date of Patent: Apr. 16, 2013

(54) MOTION CORRECTION OF SPECT IMAGES

(75) Inventors: Jonathan Sachs, Haifa (IL); Lana Volokh, Haifa (IL); Yaron Hefetz, Herzeliya (IL)

(73) Assignee: General Electric Company, Schenectady, NY (US)

( * ) Notice: Subject to any disclaimer, the term of this patent is extended or adjusted under 35 U.S.C. 154(b) by 17 days.

(21) Appl. No.: 13/165,562

(22) Filed: Jun. 21, 2011

(65) Prior Publication Data

US 2012/0326034 A1  Dec. 27, 2012

(51) Int. Cl.
*G01T 1/166* (2006.01)
(52) U.S. Cl.
USPC .............. 250/363.04; 250/336.1; 250/363.01; 250/363.02; 250/363.03
(58) Field of Classification Search ............... 250/336.1, 250/363.04
See application file for complete search history.

(56) References Cited

U.S. PATENT DOCUMENTS

| | | | |
|---|---|---|---|
| 6,242,745 B1 | 6/2001 | Berlad et al. |
| 6,388,258 B1 | 5/2002 | Berlad et al. |
| 7,332,724 B2 | 2/2008 | Hefetz et al. |
| 7,408,163 B2 | 8/2008 | Hefetz |
| 7,495,225 B2 | 2/2009 | Hefetz et al. |
| 7,514,885 B2 | 4/2009 | Hausner et al. |
| 7,531,807 B2 | 5/2009 | Hefetz |
| 7,557,352 B2 | 7/2009 | Hefetz |
| 7,592,596 B2 | 9/2009 | Klein et al. |
| 7,592,597 B2 | 9/2009 | Hefetz et al. |
| 7,671,331 B2 | 3/2010 | Hefetz |
| 7,676,869 B2 | 3/2010 | Zelnik et al. |
| 7,693,565 B2 | 4/2010 | Shai et al. |
| 7,723,688 B2 | 5/2010 | Hefetz |
| 8,022,357 B2 | 9/2011 | Amir et al. |
| 8,067,744 B2 | 11/2011 | Blevis et al. |
| 8,126,537 B2 | 2/2012 | Yakubovsky et al. |
| 2008/0226149 A1* | 9/2008 | Wischmann et al. ......... 382/131 |
| 2008/0304619 A1 | 12/2008 | Blevis et al. |
| 2009/0310825 A1* | 12/2009 | Bontus et al. ................. 382/107 |
| 2010/0166274 A1* | 7/2010 | Busch et al. .................. 382/131 |
| 2011/0044524 A1* | 2/2011 | Wang et al. ................... 382/131 |

OTHER PUBLICATIONS

U.S. Appl. No. 13/165,527, filed Jun. 21, 2011, Jonathan Sachs.
U.S. Appl. No. 13/019,590, filed Feb. 2, 2011, Bouhnik.

* cited by examiner

*Primary Examiner* — David Porta
*Assistant Examiner* — Marcus Taningco
(74) *Attorney, Agent, or Firm* — Fletcher Yoder, P.C.

(57) ABSTRACT

The present disclosure relates approaches for removing or reducing the effects of motion in parallel and non-parallel data acquisitions using a nuclear medicine imaging system. In certain embodiments, translation vectors are derived based on a registration performed on transaxial slices generated from the acquired projection data. The translation vectors may be employed to update a system matrix such that images generated using the updated system matrix are free or motion artifacts or have reduced motion artifacts.

20 Claims, 4 Drawing Sheets

PATIENT MOTION:

EQUIVALENT SITUATION EXPRESSED AS DETECTOR MOTION

MOTION CORRECTION OF SPECT IMAGES

BACKGROUND OF THE INVENTION

The subject matter disclosed herein relates to nuclear imaging, and more particularly to correction of motion artifacts in single photon emission computed tomography (SPECT).

A variety of imaging techniques are known and currently in use, such as for medical diagnostic applications. Certain such techniques, such as SPECT, rely on the emission of gamma rays during the radioactive decay of a radioisotope (or radionuclide), commonly administered in the form of a radiopharmaceutical agent that can be carried, and in some cases, be accumulated in or bound to particular tissues of interest. Such nuclear imaging technologies detect the emissions via a suitable gamma radiation detector. In particular, a suitable gamma radiation detector may consist of components which, in response to incident radiation, generate image data related to the quantity of radiation impacting the individual regions of the detector. The image data generated by the detector components may then be reconstructed to generate images of internal structures of the subject.

While such systems have proven extremely useful at providing high quality images with good diagnostic value, further refinement is possible. For example, in some instances motion artifacts may be introduced due to patient motion within the field of view and/or due to the motion of components of the imaging system during the acquisition of image data. In certain gamma ray detection configurations where non-parallel collimation techniques are employed, such motion may be difficult to address and may, therefore, lead to visual artifacts in images generated using the acquired image data.

BRIEF DESCRIPTION OF THE INVENTION

The present disclosure relates to approaches by which motion correction in SPECT images may be achieved. In one embodiment, the translational displacements of the acquired object (e.g., patient) may be addressed for both parallel and non-parallel acquisition systems. In one such embodiment, translation and duration information may be determined for a set of acquired projections, and an updated system matrix may be generated based on the translation and duration information. The updated system matrix may then be used to generate an image in which artifacts attributable to motion are reduced or eliminated.

In accordance with one aspect of the present disclosure, an image reconstruction method is provided. In accordance with this method, a set of projection data is acquired at a plurality of views and time intervals with respect to an imaging volume. A plurality of slices are reconstructed based on the set of projection data and a system matrix associated with the acquisition of the set of projection data. The slices are registered to generate a plurality of transformation vectors describing the translation in three-dimensional space for each time interval during the acquisition of the set of projection data. One or more transformation vectors are determined based on the act of registering the slices. An updated system matrix is generated based on the one or more transformation vectors and the associated time intervals. A motion-corrected image is reconstructed using the updated system matrix.

In accordance with another aspect, one or more machine readable media are provided that encode routines. The routines when executed by a processor, cause acts to be performed that include: reconstructing a plurality of slices based on a set of projection data acquired at a plurality of views and time intervals and a system matrix associated with the acquisition of the set of projection data; generating a plurality of transformation vectors describing the translation in three-dimensional space for each time interval during the acquisition of the set of projection data; determining one or more translational offsets based on the plurality of transformation vectors; and generating an updated system matrix that apply the translational offsets to one or more virtual detectors that correspond to different exposure times during the acquisition of the set of projection data.

In accordance with a further aspect, an image analysis system is provided. The image analysis system includes one or more processing components configured to receive measured projections of an imaging volume acquired at different views and time intervals with respect to the imaging volume, and to execute one or more executable routines stored in a memory. The stored routines, when executed, reconstruct a plurality of slices based on the set of projection data and a system matrix associated with the acquisition of the set of projection data, register the slices to generate a plurality of transformation vectors describing the translation in three-dimensional space for each time interval during the acquisition of the set of projection data, and generate an updated system matrix based on the plurality of transformation vectors and corresponding time intervals. The image analysis system also includes interface circuitry configured to allow user interaction with the image analysis system.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

As discussed herein, the present disclosure relates to the generation of nuclear medicine images, such as SPECT reconstructions, in which artifacts attributable to motion are reduced or removed. For example, in one embodiment, a system matrix that describes or corresponds to the physical camera geometry with respect to the imaging volume may be modified to correspond to two or more positions of the patient and/or camera during image acquisition. The modified system matrix may then be used in the reconstruction of the acquired image data such that image data associated with each modeled position or geometry is properly reconstructed with the differences in geometry being reduced or removed. In this manner, artifacts attributable to motion may be reduced or eliminated, even in system where a non-parallel detector mechanism is employed.

Figure 1:
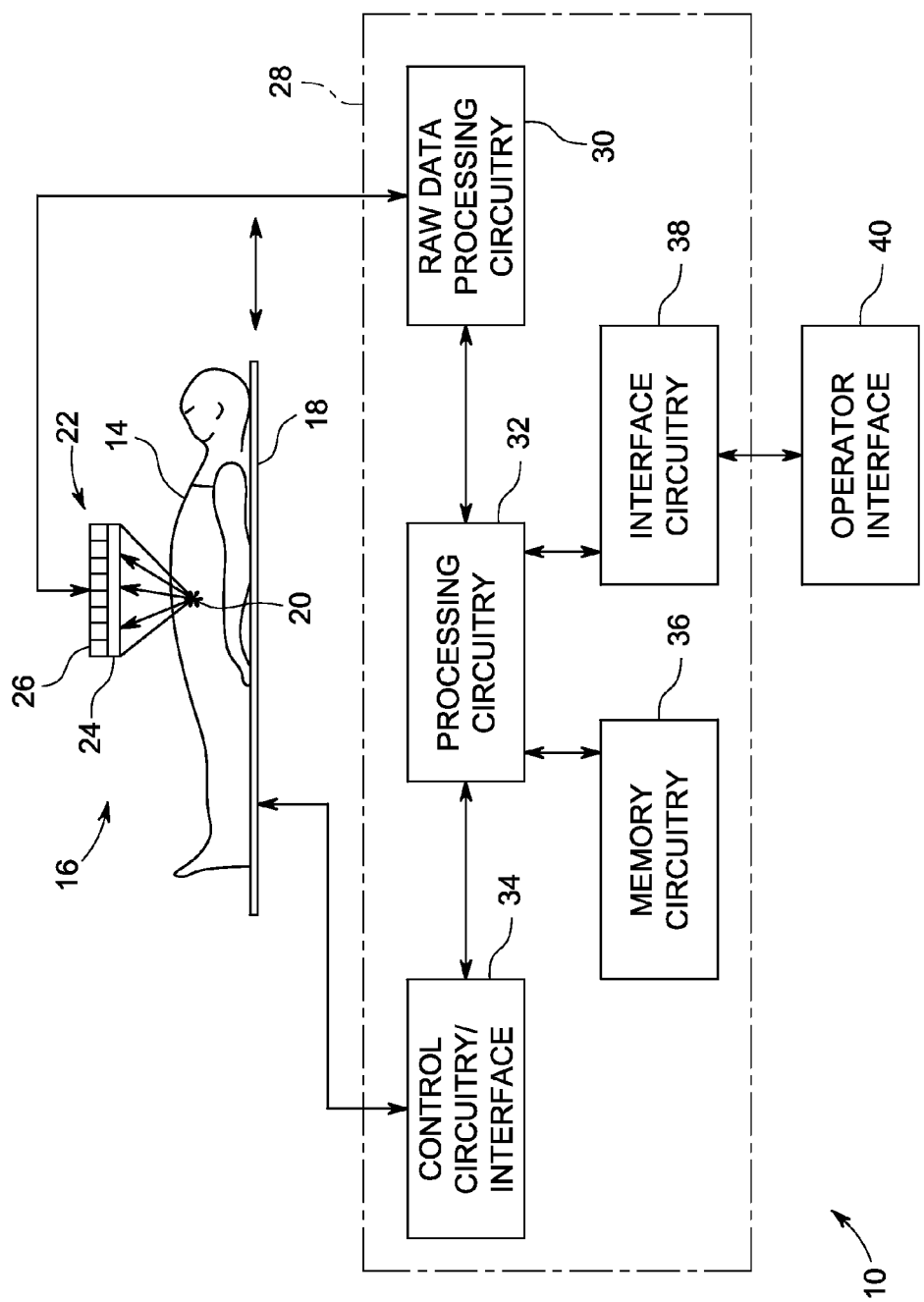
FIG. 1 is a diagrammatical representation of an embodiment of a SPECT imaging system suitable for use in accordance with the present disclosure.

With the foregoing discussion in mind, a diagrammatic representation of one example of a SPECT imaging system suitable for use with the present approach is shown in FIG. 1. The system of FIG. 1, designated generally by the reference numeral 10, is designed to produce useful images of a subject 14 using suitable detector components (such as pin-hole gamma cameras or collimated scintillating detectors) as described in detail below. The subject is positioned in a scanner, designated by reference numeral 16, in which a patient support 18 is positioned. The support may be movable within the scanner to allow for imaging of different tissues or anatomies of interest 20 within the subject. Prior to image data collection, a radioisotope, such as a radiopharmaceutical substance (sometimes referred to as a radiotracer), is administered to the patient, and may be bound or taken up by particular tissues or organs 20. Typical radioisotopes include various radioactive forms of elements that emit gamma radiation during decay. Various additional substances may be selectively combined with such radioisotopes to target specific areas or tissues 20 of the body.

Gamma radiation emitted by the radioisotope is detected by a detector component 22, such as a digital detector or gamma cameras. Although illustrated in the figure as a planar device positioned above the patient to simplify illustration, in practice the detector structure(s) 22 may be positioned about the patient, such as in an arc or ring about the patient, or may be attached to a positioner (e.g., a C-arm, gantry, or other movable arm) that allows the detector structure(s) 22 to be moved in such an arc or orbit about the patient during data acquisition. In general, the detector structure(s) 22 typically include one or more components or elements capable of sensing gamma radiation or otherwise generating a detectable signal in response to such radiation. In the illustrated embodiment, the detector structures comprise one or more collimators and a scintillator, together represented generally as reference numeral 24. The collimator may be formed from parallel or non-parallel elements that allow gamma radiation emitted only in certain directions to impact the detecting components. In detector embodiments employing a scintillator, the scintillator may be made of a crystalline material, such as sodium iodide (NaI), that converts the received gamma radiation to lower energy light energy (e.g., in an ultraviolet range). Photomultiplier tubes 26 then receive this light and generate image data corresponding to photons impacting specific discrete picture element (pixel) regions. In other embodiments, the detector structure 22 may not be collimated but may instead use other gamma radiation sensing technologies, such as one or more pin-hole gamma cameras, as also discussed herein.

In the depicted embodiment, the detector structure(s) 22 is coupled to system control and processing circuitry 28. This circuitry may include a number of physical and/or software components that cooperate to allow the collection and processing of image data to create the desired images. For example, the circuitry may include raw data processing circuitry 30 that initially receives the data from the detector structure(s) 22, and that may perform various filtering, value adjustments, and so forth. Processing circuitry 32 allows for the overall control of the imaging system, and for manipulation and/or reconstruction of image data. The processing circuitry 32 may also perform calibration functions, correction functions, and so forth on the data. The processing circuitry 32 may also perform image reconstruction functions, such as based on known algorithms (e.g., back projection, iterative reconstruction, and so forth). Such functions may also be performed in post-processing on local or remote equipment. As will be appreciated, the various image reconstruction and artifact correction algorithms discussed herein may be implemented in part or in their entirety using one or both of the raw data processing circuitry 30 and/or the processing circuitry 32.

In the depicted embodiment, the processing circuitry 32 interacts with control circuitry/interface 34 that allows for control of the scanner and its components, including the patient support, camera, and so forth. Moreover, the processing circuitry 32 will be supported by various circuits, such as memory circuitry 36 that may be used to store image data, calibration or correction values, routines performed by the processing circuitry (such as the motion artifact correction algorithms disclosed herein), and so forth. In one embodiment, the processing circuitry executes one or more iterative reconstruction algorithms that may utilize approaches for reducing or removing motion effects, as discussed herein. Such iterative reconstruction approaches may generally utilize iterated comparisons between expected or reference images and observed or measured image data to reduce artifacts or irregularities attributable to non-physiological factors, such as factors related to motion and/or imaging system geometry. In such an iterative reconstruction approach, the convergence process or loop may be repeated or iterated until some completion criteria is met, such as minimization of a cost function.

Finally, the processing circuitry may interact with interface circuitry 38 designed to support an operator interface 40. The operator interface allows for imaging sequences to be commanded, scanner and system settings to be viewed and adjusted, images to be viewed, and so forth. In the illustrated embodiment, the operator interface includes a monitor 42 on which reconstructed images 12 may be viewed.

In an institutional setting, the imaging system 10 may be coupled to one or more networks to allow for the transfer of system data to and from the imaging system, as well as to permit transmission and storage of image data and processed images. For example, local area networks, wide area networks, wireless networks, and so forth may allow for storage of image data on radiology department information systems and/or on hospital information systems. Such network connections further allow for transmission of image data to remote post-processing systems, physician offices, and so forth.

With respect to the gamma ray detection components 22 of the SPECT imaging system 10, two arrangements are used: parallel and non-parallel. In an example of a parallel arrangement, a detector may be collimated with an arrangement of parallel structures such that the resulting acquisition of gamma rays is not divergent. For example, turning to FIG. 2, a collimated detector assembly 60 or collimated camera is employed and is depicted at four different radial views (A-D) with respect to the patient 14. In one such arrangement, image data is sequentially acquired, with the detector components being rotated to the different radial positions (A-D) at discrete points in time to acquire image data at the respective radial views. The collimator in such an assembly 60 acts to limit the angular range of gamma rays striking the detector panel (i.e., gamma rays striking a detector panel at a given radial view are substantially parallel to one another), thereby helping to localize the gamma ray emission. Thus, in such an image acquisition configuration, the collimated detector assembly 90 has a parallel field-of-view 62 that is limited, non-inverted, and which does not expand with distance, i.e., does not diverge.

This arrangement is in contrast to detector arrangements where the employed collimation is non-parallel such as pin-hole collimator, fan-beam collimator, or cone-beam collimator. For example, FIG. 3 depicts a pin-hole camera 70 or multiple pin-hole cameras 70 at different radial views (A-D) with respect to the patient 14. In one such arrangement, image data is sequentially acquired, by one or more pin-hole cameras 70 being rotated to the different radial positions (A-D) at discrete points in time to acquire image data at the respective radial views. In contrast to the parallel collimated arrangement of FIG. 2, in the depicted pin-hole camera 70 arrangement a pin-hole camera 70 has an associated non-parallel field-of-view 72 from a given view angle, as depicted by respective dashed lines, that diverges with distance. Thus, as will be appreciated, pin-hole cameras 70, such as those depicted, and other non-parallel acquisition systems generally acquire conical projections corresponding to an inverted image of the non-parallel field-of-view 72 associated with the respective camera 70.

With respect to the use of fan-beam and cone-beam collimators, the non-parallel field-of-view 72 is actually converging in two-dimensions or three-dimensions to a line or a point respectively. In such instances, the focal line or point may be within the volume of the patient. Similar situations may also exist in computed tomography (CT) where a volume is imaged. In some instances, a CT imager may comprise a slow rotating gantry, such as a C-arm. The focal point of the field-of-view of the associated two-dimensional detector array is the X-ray source (e.g., an X-ray tube). While the present discussion focuses primarily on SPECT systems in order to provide a useful context and easily visualized examples, it should be understood that other types of imaging modalities that are susceptible to patient motion, such as CT, positron emission tomography (PET), magnetic resonance imaging (MRI), and others, may also benefit from the patient motion correction approach disclosed herein.

As previously noted, over the course of an examination, the patient (or internal organs of the patient) may move with respect to the acquisition imaging geometry, regardless of type. Likewise, imaging geometry changes with respect to the region or organ of interest due to the movement of the detector components about the patient may result in perceived motion. In conventional systems, correction for such motion effects may be based on detection of translational displacements of projections relative to a reference. For example, a forward projection of a reconstructed image may be compared to a previous projection employed as a reference, with differences between the images being attributed to a translational displacement. Once detected, the projection may be translated back to the expected, i.e., motion free, location. Such corrections may be iteratively performed.

Figure 2:
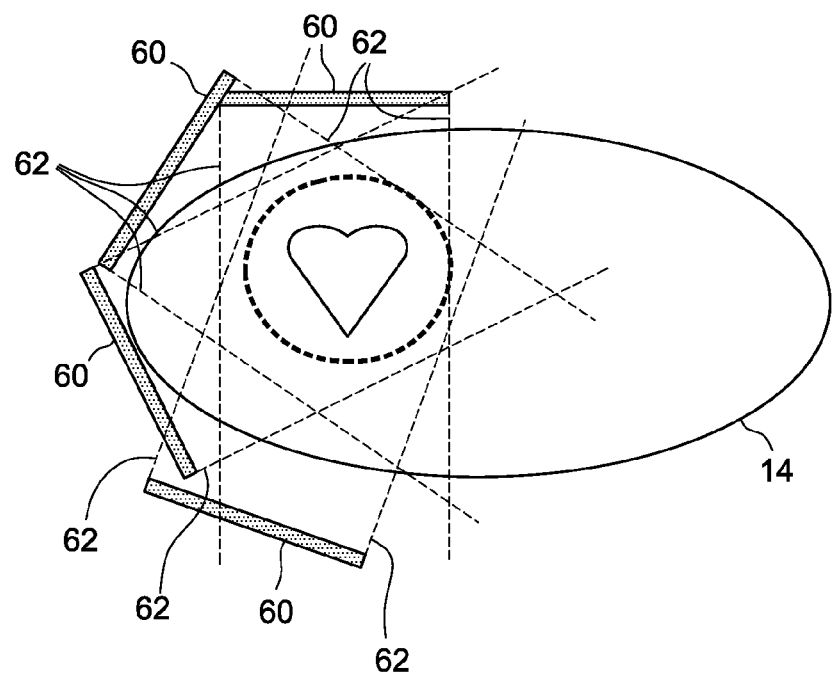
FIG. 2 depicts an example of a SPECT image acquisition occurring over a variety of views using collimated gamma detector assembly, in accordance with aspects of the present disclosure.
Figure 3:
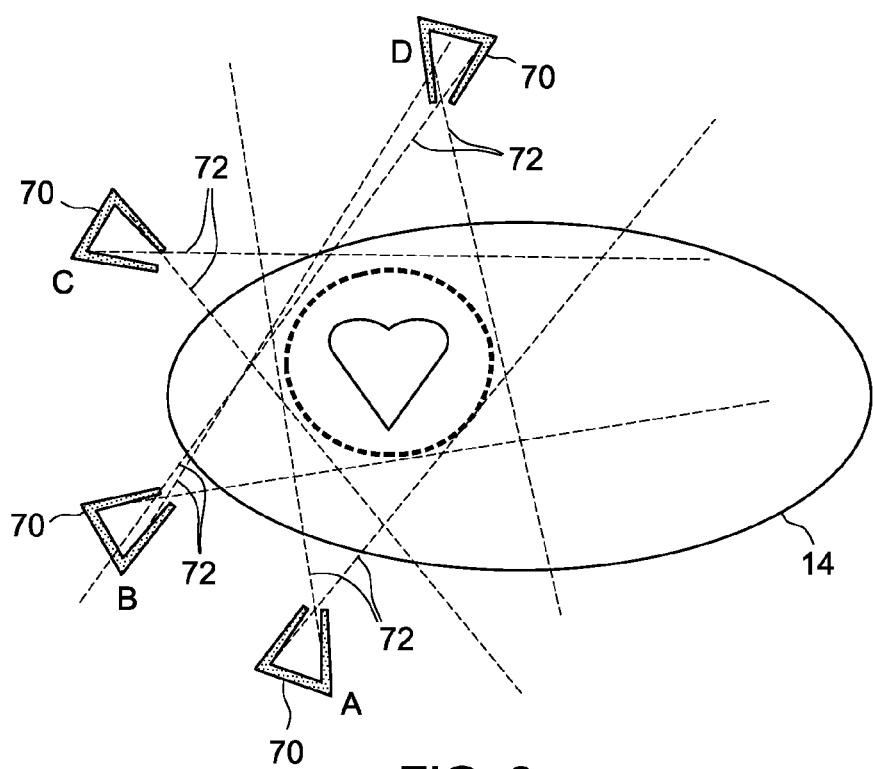
FIG. 3 depicts an example of a SPECT image acquisition occurring over a variety of views using pin-hole camera type gamma detectors, in accordance with aspects of the present disclosure.

Such conventional motion correction may be sufficient for parallel shift variant projections, such as where parallel collimation of the detector is employed, as in FIG. 2. However, non-parallel shift variant projections (e.g., pin-hole camera and/or detector assemblies employing diverging or converging collimators or FOVs) may include motion components arising from non-translational transformations of the projections. Such non-translation transformation cannot be corrected without knowledge of the three-dimensional distribution of the data. That is, the non-parallel aspects of the acquired projections result in perceived or observed motion or differences that are not simply translations of the data in one direction or another, but are instead other transformations of the data, such as perceived changes in shape or size. For example, it is evident that a rigid translation motion of an organ away from a pinhole collimator will cause a general reduction of the size of its image on the detector, yet different parts of the organ will be differently distorted depending on their exact spatial location in relation to the pinhole. Similarly, any motion, axial or lateral, of an imaged object would cause a non-linear distortion of the projected image.

Figure 4:
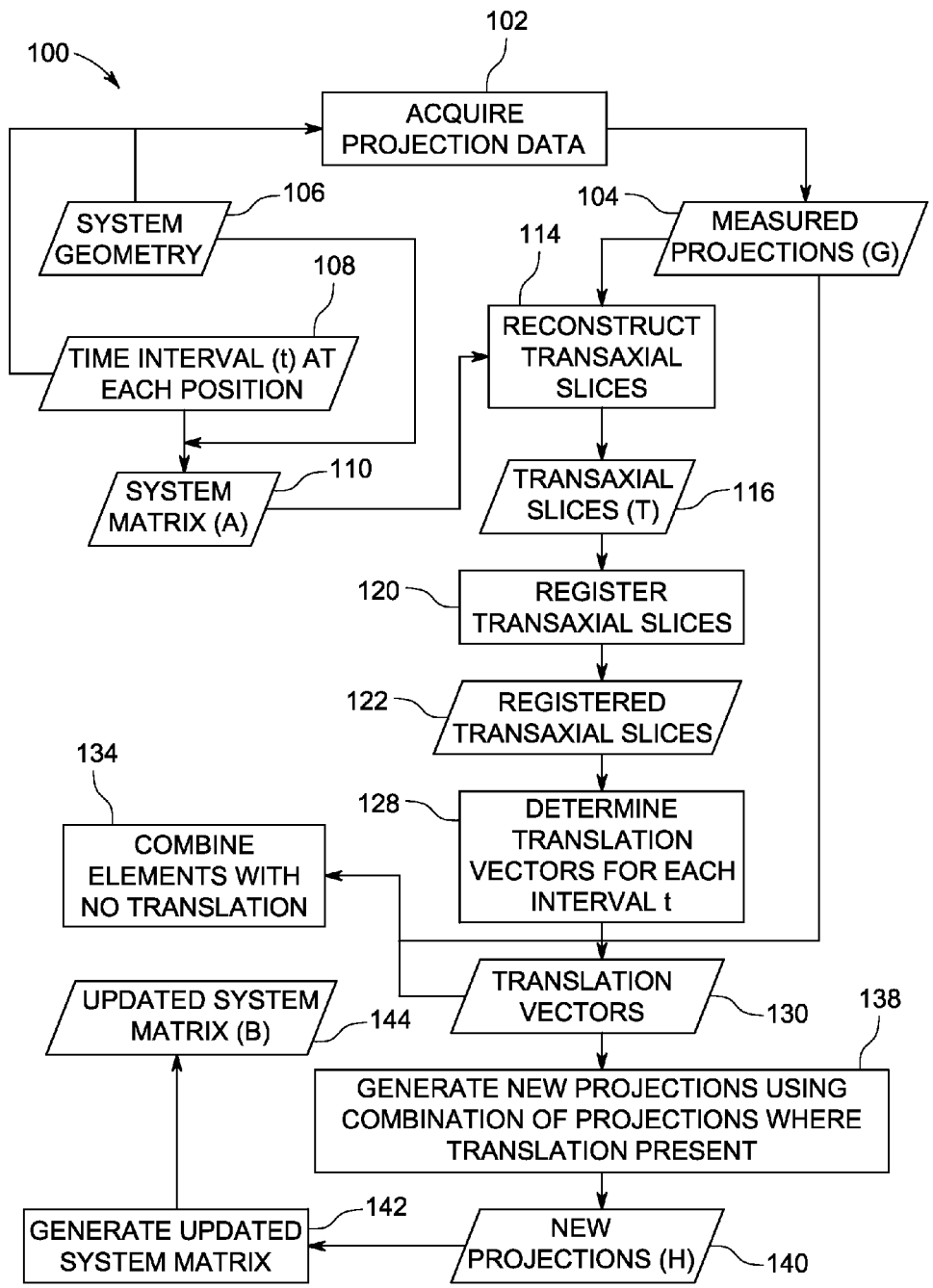
FIG. 4 depicts a flow diagram of processor-executable logic for addressing motion artifacts in SPECT images, in accordance with aspects of the present disclosure.

Turning to FIG. 4, a flowchart is provided depicting control logic for correcting for motion effects even in a non-parallel data acquisition, such as those depicted in the system of FIG. 3. While the described approach is suitable for motion correction in such a non-parallel system, the approach is also suitable for use with data collected using a parallel acquisition system, as depicted in FIG. 2.

In the depicted flowchart 100, a step of acquiring (block 102) a set of multiple projections (G) 104 of elements $G_i$ is depicted. Each projection is typically derived or generated over a non-overlapping time interval (t) 108, such as a time interval of 20 seconds. In one embodiment, the set of projection data 104 represents sequential acquisitions of projections over non-overlapping time intervals of length t.

The acquisition step includes both spatial and temporal variables, denoted by system geometry 106 and time intervals (t) 108 which respectively describe the spatial and geometric relationship between the detector and the imaged volume during different aspects of the acquisition process and the time intervals associated with each geometric configuration of the system. The system geometry 106 and associated time intervals 108 of the data acquisition may define or be used to generate a system matrix (A) 110 that describes the relationship between elements of the detector(s) that generate a signal and voxels within the imaging volume at specified times. In one embodiment, system matrix 110 may be provided as a table (e.g., a correlation table) or other data structure that describes the relationship at specified times between what signal or value would be observed at a detector element based on the activity or intensity (e.g., emitted radiation) at a given voxel of the imaging volume. That is, the system matrix describes the relationship between activity within the imaging volume and expected observations at the detector for a given geometry and at a given time.

In the depicted example, each element (i.e., G) of the set of projections 104 is reconstructed (block 114) to generate respective transaxial slices (T) 116. The reconstruction process, in one embodiment, is based on the system matrix 110 such that:

$$A * T_i = G_i \quad (1)$$

where A is the system matrix, $G_i$ is a projection or element of the set of projections 104, and $T_i$ is a transaxial slice generated based on G.

The transaxial slices 116 may be registered (block 120) against a baseline or reference transaxial slice to generate a plurality of registered transaxial slices 122. In one embodiment the registration uses a translation or vector transformation with a metric (e.g., cross-correlation, mutual information, least mean squares, and so forth). In one embodiment, the elements of transaxial slices $T_i$ where i>0 may be registered against the elements of a first or baseline transaxial slice $T_0$. Registration against the baseline or reference transaxial slice allows determination (block 128) of the respective transformation vectors TR 130 ($tr_x$, $tr_y$, $tr_z$) describing the translation (lateral movement and/or rotational movement) of elements or structures in three-dimensional space for each time interval during the acquisition.

For elements where there was no translation is space or time during the acquisition process, a combination may be performed (block 134) to simplify subsequent computations. However, for those elements where a translation (lateral movement or rotational) is determined to be present, a new set of projections (H) 140 may be generated (block 138) using a combination of all projections where there is a given translational offset. In one such embodiment, the number of new projections is the product of the number of translational offsets by the number of original projections. That is, projection data may be binned together based on the absence of movement (i.e., no translation from the reference) and/or where the movement is the same so that all projections to be corrected based on a given translation may be binned together.

Based on the translation and duration of the projections associated with each set of new projections H 140 and using the system matrix A which maps $G_t$ to T such that $A*T=G$ (see equation 1) an updated system matrix B 144 may be generated (block 142). For example, in one implementation, the updated system matrix B 144 may describe a relationship where:

$$B*T=H \qquad (2)$$

In one implementation, the generation of the updated system matrix B 144 may be simplified by assuming a translation in steps of whole voxels. Effectively, in this manner, the updated system matrix is modified or updated to represent the various geometries or relative camera positions present in the data acquisition step and the corresponding observed projection data is essentially binned based on time and camera geometry.

Because the updated system matrix 144 takes into account the observed motion and corresponding time data for when motion is observed, the projection data 104 itself may be unmodified as the necessary motion compensation is provided for by the corresponding elements of the updated system matrix 144. The updated system matrix 144 may be used to reconstruct the entire projection data set to generate a motion-free or motion-reduced image using methods that utilize a system matrix in the reconstruction process, such as maximum likelihood expectation maximization (MLEM), ordered subsets expectation maximization (OSEM), block sequential regularized expectation maximization (BSREM), and so forth. In particular, the updated system matrix 144 may be used to reconstruct a motion-free or motion-reduced image even in situations where the data acquisition involved the use of a non-parallel detection scheme (i.e., pin-hole cameras or divergent or convergent collimation schemes.).

Figure 5:
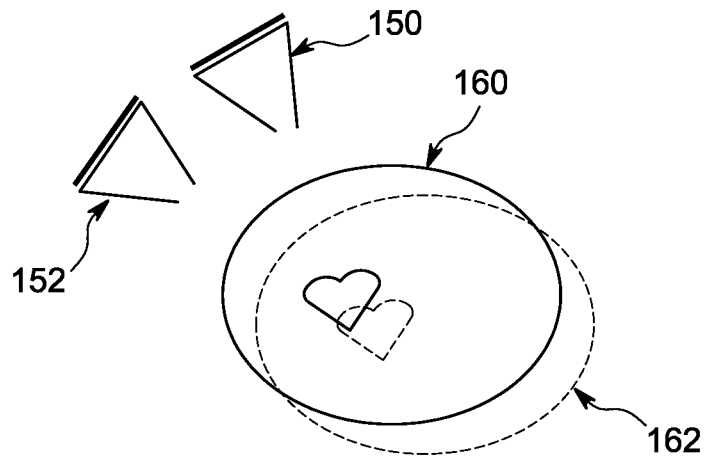
FIG. 5 depicts an example of a motion correction operation performed on the measured data, in accordance with one aspect of the present disclosure.

With the foregoing discussion in mind, a simplified example is provided to assist in visualizing motion and motion correction as presently contemplated. Turning to FIG. 5, an incidence of undesired patient motion during a multi pin-hole camera image acquisition process is depicted. In this example, the undesired motion occurs at time $t_1$ such that projection data acquired by a first detector A 150 and a second detector B 152 during first the time interval between $t_0$ and $t_1$ corresponds to the patient being at a first position. Similarly, projection data acquired during a second time interval between $t_1$ and $t_T$ by the first detector A 150 and the second detector B 152 corresponds to the patient being at a second position. With the foregoing in mind, it will be appreciated that four different data sets are derived in this simplified example: $D_{A1}$ corresponding to the data acquired by first detector 150 between $t_0$ and $t_1$; $D_{B1}$ corresponding to the data acquired by second detector 152 between $t_0$ and $t_1$; $D_{A2}$ corresponding to the data acquired by first detector 150 between $t_1$ and $t_T$; and $D_{B2}$ corresponding to the data acquired by second detector 152 between $t_1$ and $t_T$. As will be appreciated, reconstructing the entire data set acquired by the detectors 150, 152 between $t_0$ and $t_T$ will yield a blurred image due to the change in patient position within this time interval.

In accordance with previous approaches, the datasets acquired at the different time intervals (i.e., datasets $D_{A1}$ and $D_{B1}$ corresponding to $t_0$ to $t_1$ and datasets $D_{A2}$ and $D_{B2}$ corresponding to $t_1$ to $t_T$) are separately reconstructed to obtain two translated images: first image ($P_1$) 160 and second image ($P_2$) 162. In performing this reconstruction, system matrix $M_A$ and $M_B$ may be used to represent the first detector 150 and the second detector 152 respectively such that:

$$(D_{A1})(M_A)+(D_{B1})(M_B) \rightarrow P_1; \text{ and} \qquad (3)$$

$$(D_{A2})(M_A)+(D_{B2})(M_B) \rightarrow P_2. \qquad (4)$$

In accordance with previous approaches, second image $P_2$ 162 is offset with respect to image $P_1$ 160 due to patient or other motion. The second image $P_2$ 162 may be translated by a translation vector "Tr" such that the two images are correctly registered, i.e., aligned, where $$(Tr)(P_2) \rightarrow P_2'. \qquad (5)$$

Once registered, P1 and $P_2'$ may be summed to get a final image:

$$P1+P_2' \rightarrow P'. \qquad (6)$$

As noted previously, this previously known approach may yield sub-optimal results since each dataset contains less detected gamma events, resulting in $P_1$ 160 and $P_2$ 162 having high levels of statistical noise.

It should be noted that iterative algorithms are mathematically non-linear in the sense that adding reconstruction results of several data sub-sets is not the same as adding the data sub-sets and then reconstructing. In linear reconstruction algorithms such as Filter Back Projection (FBP), the order of summing is not important. Image quality of iterative reconstruction of correctly summed data sub-sets may thus be superior to the results of summating of results of iterative reconstruction of each sub-set separately. It is the deformation caused by the non parallel nature of the camera that prevents simple translation and summation of the data sub-sets and requires creating a compensating system matrix to allow iterative reconstruction of the entire data set.

Figure 6:
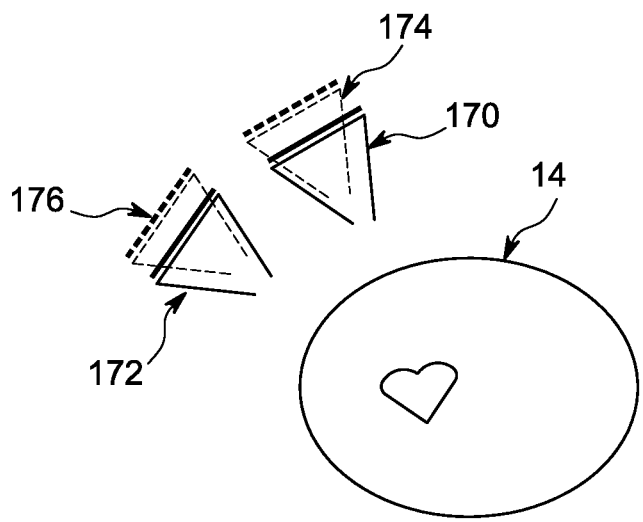
FIG. 6 depicts an example of a motion correction operation performed on the system geometry, e.g., system matrix, in accordance with one aspect of the present disclosure.

Turning to FIG. 6, and in accordance with certain present embodiments, the parameters of the patient translation Tr may be used in an alternative manner for motion correction. For example, in the depicted implementation the detection system (i.e., first detector 150 and second detector 152) is virtually translated such that the patient remains stationary. It should be understood that, as used herein, a translation may be a rigid translation or lateral move, a rigid rotation, or a combination or lateral and rotational moves.

In this example, this would result in two sets of detectors (i.e., four virtual detectors in this example) being obtained, with each virtual detector characterized by its coordinates and exposure time. In this example, the four virtual detectors may be characterized as: virtual detectors A1 170 and B1 172 that acquired data during the first time interval $t_0$ to $t_1$ and virtual detector A2' 174 and B2' 176 that acquired data during the second time interval and where A2' 174 and B2' 176 are translated by (−Tr), i.e., negatively translated). In view of the use of the virtual detectors characterized in coordinates and exposure time, the datasets associates with each virtual detector may be described as: datasets $D_{A1}$ corresponding to detector A1 170 at $t_0$ to $t_1$, $D_{B1}$ corresponding to detector B1 172 at $t_0$ to $t_1$, $D_{A2}$ corresponding to detector A2' 174 at $t_1$ to $t_T$, $D_{B2}$ corresponding to detector B2 176 at $t_1$ to $t_T$. As will be appreciated, the datasets are not shifted due, instead, to the appropriate virtual detectors (e.g., A2' and B2') being shifted.

Based on this virtualized detection system, a new composite system matrix (i.e., updated system matrix 144) may be characterized for the four virtual detectors of this example. For example the new composite system matrix may be comprised of system matrices $M_A$, $M_A'$, $M_B$, and $M_B'$ which each take into account the appropriate translated or untranslated system geometry and appropriate acquisition time for each interval $t_0$ to $t_1$ and $t_1$ to $t_T$. As discussed above, the new composite system matrix may be used to reconstruct the entire dataset to get an improved final image P":

$$(D_{A1})(M_A)+(D_{A2})(M_A')+(D_{B1})(M_B)+(D_{B2})(M_B') \rightarrow P''. \quad (7)$$

It should be understood that, though the preceding example related to only two time intervals to simplify explanation, the presently disclosed approach may be applied to more than two time intervals. For example, in one implementation acts may be performed to identify the various times associated with patients motions and to construct the appropriate time intervals based on the observed patient motion. In one such implementation, the total time $t_0$ to $t_T$ may be divided into N intervals (e.g., 0-dt, dt-2dt, 2dt-3dt, ..., (N−1)dt-T, where dt=T/N). Reconstruction may performed for each interval separately, as discussed above, and the reconstructed images may be analyzed (such as by registration to a reference) to identify instances of motion.

If there was only one instance of patient motion (such as at t(i)~dt*i t(i)), image shifts Tr are given by:

$$Tr1=Tr2=\ldots Tr(i)=0; \quad (8)$$

$$Tr(i+1)\sim \ldots \sim Tr(N) \sim Tr(\text{motion}); \quad (9)$$

where Tr(motion) is the motion of the patient at time dt*i. The total acquired data can now be split between two intervals, 0-dt*I and dt*i-T, since there was only one instance of motion (i.e., pre-motion data and post-motion data). Alternatively, in other implementations an external and/or independent motion detection mechanism may be employed to detect one or more instances of patient motion. When the time or times that the motions occurred is known, the process may be carried out as discussed above On example of an implementation in which the present approach may be applied is in the field of cardiology. For example, after a cardiac stress test (in which the patient performs a strenuous physical exercise to increase the heart rate) the heart shifts from its rest position, and, during recovery, slowly moves back toward its rest position. In such an instance, Tr is a function of time. For example, Tr(at time t=i*dt) is given by Tr(dt*i)=dTr*i or if a non linear translation is assumed Tr(dt*i)=dTr*i+ddTr*i*i.

In this cardiology example, the times associated with patient motion (here heart motion) may be used to determine $TR_1$, $TR_2$, ... $TR_N$, and so forth that describe the lateral motion and/or rotation of the heart in each time interval that is identified as including motion. Once the respective translation factors, $TR_1$, $TR_2$, ... $TR_N$, are known, these translation factors may be fitted to the preceding equation to determine dTr (and optionally ddTr). A new composite system matrix may then be constructed with the (now known) translations given by Tr(dt*i)=dTr*i or Tr(dt*i)=dTr*i+ddTr*i*i. The new composite system matrix may then be used to reconstruct the entire image dataset to generate an improved, motion-corrected image.

Technical effects of the invention include generation of a reconstructed volume in which the effects of motion are reduced or eliminated. Technical effects may include acquiring projection data using a non-parallel detector architecture and generating motion-free or motion-reduced images based on the acquired projection data. Technical effects may also include generation of an updated system matrix based at least on transformation information obtained from transaxial slices reconstructed from measured projection data.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An image reconstruction method, comprising the acts of:
    acquiring a set of projection data at a plurality of views and time intervals with respect to an imaging volume;
    reconstructing a plurality of slices based on the set of projection data and a system matrix associated with the acquisition of the set of projection data;
    registering the slices to generate a plurality of transformation vectors describing a respective translation in three-dimensional space for each time interval during the acquisition of the set of projection data;
    determining one or more transformation vectors based on the act of registering the slices;
    generating an updated system matrix based on the one or more transformation vectors and the associated time intervals; and
    reconstructing a motion-corrected image using the updated system matrix.

2. The image reconstruction method of claim 1, wherein the set of projection data comprises a set of single photon emission computed tomography (SPECT) projection data.

3. The image reconstruction method of claim 1, wherein the set of projection data is acquired at a variety of view angles and time intervals with respect to the imaging volume.

4. The image reconstruction method of claim 1, wherein the system matrix describes one or both of a system geometry or time intervals at different imaging positions associated with the acquisition of the set of projection data.

5. The image reconstruction method of claim 1, wherein the slices comprise transaxial slices.

6. The image reconstruction method of claim 1, wherein registering the slices comprises registering the slices against a baseline or reference slice.

7. The image reconstruction method of claim 1, comprising combining elements where a translational offset is not determined to be present based on the act of registering the slices.

8. The image reconstruction method of claim 1, wherein the registration uses a translation of vector transformation.

9. The image reconstruction method of claim 1, wherein the updated system matrix corresponds to a two or more virtual detectors, each characterized by a position and an exposure time.

10. The image reconstruction method of claim 1, wherein the set of projection data is acquired using a non-parallel detector geometry.

11. The image reconstruction method of claim 10, wherein the non-parallel detector geometry is associated with one or more of a pin-hole camera, a convergently collimated detector, or a divergently collimated detector.

12. One or more non-transitory machine readable media encoding routines that, when executed by a processor, cause acts to be performed comprising:
- reconstructing a plurality of slices based on a set of projection data acquired at a plurality of views and time intervals and a system matrix associated with the acquisition of the set of projection data;
- generating a plurality of transformation vectors describing a respective translation in three-dimensional space for each time interval during the acquisition of the set of projection data;
- determining one or more translational offsets based on the plurality of transformation vectors; and
- generating an updated system matrix that applies the translational offsets to one or more virtual detectors that correspond to different exposure times during the acquisition of the set of projection data.

13. The one or more non-transitory machine readable media of claim 12, wherein the plurality of transformation vectors are generated based upon a registration operation performed on the plurality of slices.

14. The one or more non-transitory machine readable media of claim 12, wherein the system matrix describes one or both of a system geometry or time intervals at different imaging positions associated with the acquisition of the set of projection data.

15. The one or more non-transitory machine readable media of claim 12, wherein the one or more machine readable media encode routines that, when executed by a processor, cause acts to be performed comprising combining elements where a translational offset is not determined to be present.

16. An image analysis system, comprising:
- one or more processing components configured to receive measured projections of an imaging volume acquired at different views and time intervals with respect to the imaging volume, and to execute one or more executable routines stored in a memory;
- the memory storing the one or more executable routines, wherein the stored routines, when executed, reconstruct a plurality of slices based on the set of projection data and a system matrix associated with the acquisition of the set of projection data, register the slices to generate a plurality of transformation vectors describing a respective translation in three-dimensional space for each time interval during the acquisition of the set of projection data, and generate an updated system matrix based on the plurality of transformation vectors and corresponding time intervals; and
- interface circuitry configured to allow user interaction with the image analysis system.

17. The image analysis system of claim 16, comprising:
- one or more detector assemblies suitable for detecting radiation emitted from a patient, wherein the one or more detector assemblies detect non-parallel radiation emissions;
- data acquisition circuitry configured to acquire signals from the one or more detector assemblies, wherein the measured projections are or are derived from the acquired signals.

18. The image analysis system of claim 17, wherein the one or more detector assemblies comprise pin-hole gamma cameras, convergently collimated detector assemblies, or divergently collimated detector assemblies.

19. The image analysis system of claim 17, comprising a positioner capable of moving the one or more detector assemblies with respect to the imaging volume.

20. The image analysis system of claim 16, wherein the registration uses a translation or vector transformation.

* * * * *